(12) United States Patent
Binette et al.

(10) Patent No.: US 8,496,970 B2
(45) Date of Patent: *Jul. 30, 2013

(54) CONFORMABLE TISSUE REPAIR IMPLANT CAPABLE OF INJECTION DELIVERY

(75) Inventors: Francois Binette, Weymouth, MA (US); Joseph J. Hammer, Bridgewater, NJ (US); Krish Mukhopadhyay, Bridgewater, NJ (US); Joel Rosenblatt, Watchung, NJ (US)

(73) Assignee: DePuy Mitek, LLC, Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/406,230

(22) Filed: Feb. 27, 2012

(65) Prior Publication Data

US 2012/0156265 A1    Jun. 21, 2012

Related U.S. Application Data

(63) Continuation of application No. 12/980,544, filed on Dec. 29, 2010, now Pat. No. 8,137,702, which is a continuation of application No. 10/723,982, filed on Nov. 26, 2003, now Pat. No. 7,316,822, and a continuation of application No. 11/947,384, filed on Nov. 29, 2007, now Pat. No. 7,875,296, which is a continuation of application No. 10/723,982, filed on Nov. 26, 2003, now Pat. No. 7,316,822.

(51) Int. Cl.
*A61K 35/32* (2006.01)

(52) U.S. Cl.
USPC .... 424/549; 424/93.7; 623/23.58; 623/23.75; 623/23.72

(58) Field of Classification Search
None
See application file for complete search history.

(56) References Cited

U.S. PATENT DOCUMENTS

| | | | |
|---|---|---|---|
| 3,272,204 A | 9/1966 | Artandi |
| 3,739,402 A | 6/1973 | Cooley et al. |
| 3,812,017 A | 5/1974 | Santangelo at al. |
| 3,857,932 A | 12/1974 | Shepherd et al. |
| 4,045,418 A | 8/1977 | Sinclair |
| 4,057,537 A | 11/1977 | Sinclair |
| 4,105,034 A | 8/1978 | Shalaby et al. |
| 4,130,639 A | 12/1978 | Shalaby et al. |
| 4,130,689 A | 12/1978 | Costa, Jr. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,344,193 A | 8/1982 | Kenny |
| 4,520,821 A | 6/1985 | Schmidt et al. |
| 4,553,272 A | 11/1985 | Mears |
| 4,597,766 A | 7/1986 | Hilal et al. |
| 4,609,551 A | 9/1986 | Caplan et al. |
| 4,728,329 A | 3/1988 | Mansat |
| 4,801,299 A | 1/1989 | Brendel et al. |
| 4,837,285 A | 6/1989 | Berg et al. |
| 4,902,508 A | 2/1990 | Badylak et al. |
| 4,917,700 A | 4/1990 | Aikins |
| 4,946,377 A | 8/1990 | Kovach |
| 5,007,934 A | 4/1991 | Stone |
| 5,041,138 A | 8/1991 | Vacanti et al. |
| 5,053,050 A | 10/1991 | Itay |
| 5,061,281 A | 10/1991 | Mares et al. |
| 5,078,744 A | 1/1992 | Chvapil |
| 5,108,989 A | 4/1992 | Amento et al. |
| 5,147,400 A | 9/1992 | Kaplan et al. |
| 5,176,708 A | 1/1993 | Frey et al. |
| 5,206,023 A | 4/1993 | Hunziker et al. |
| 5,258,028 A | 11/1993 | Ersek et al. |
| 5,263,984 A | 11/1993 | Li et al. |
| 5,306,311 A | 4/1994 | Stone et al. |
| 5,326,357 A | 7/1994 | Kandel et al. |
| 5,366,756 A | 11/1994 | Chesterfield et al. |
| 5,425,766 A | 6/1995 | Bowald et al. |
| 5,443,950 A | 8/1995 | Naughton et al. |
| 5,445,833 A | 8/1995 | Badylak et al. |
| 5,455,041 A | 10/1995 | Genco et al. |
| 5,464,929 A | 11/1995 | Bezwada et al. |
| 5,468,253 A | 11/1995 | Bezwada et al. |
| 5,480,827 A | 1/1996 | Guillemin et al. |
| 5,487,897 A | 1/1996 | Polson et al. |
| 5,514,181 A | 5/1996 | Light et al. |
| 5,514,378 A | 5/1996 | Mikos et al. |
| 5,571,189 A | 11/1996 | Kuslich |
| 5,577,517 A | 11/1996 | Bonutti |

(Continued)

FOREIGN PATENT DOCUMENTS

AU    717552 B2    3/2000
CA    2247158 A1    8/1997

(Continued)

OTHER PUBLICATIONS

Japanese Office Action issued Apr. 24, 2012 for Application No. 2007-171032 (6 Pages).
"Allcock in the Encyclopedia of Polymer Science", vol. 13, pp. 31-41, Wiley Intersciences, John Wiley & Sons, 1988.
Albrecht et al., "Closure of Osteochondral Lesions Using Chondral Fragments and Fibrin Adhesive," *Arch. Orthop. Trauma Surg.* 101: 213-217 (1983).
Albrecht. F.H., "The Closure of Joint Cartilage Defects by Means of Cartilage Fragments and Fibrin Adhesive," Fortschr. Med. 101(37):1650-52 (1983).
Andreasen et al., Evaluation of different types of autotransplanted connective tissues as potential periodontal ligament substitues: an experimental replantation study in monkeys, International Journal of Oral Surgery, Jun. 1981, vol. 10, Issue 3, pp. 189-201.(Full text).

(Continued)

*Primary Examiner* — Irene Marx
*Assistant Examiner* — Satyendra Singh (57) ABSTRACT

A conformable tissue implant is provided for use in repairing or augmenting a tissue defect or injury site. The tissue implant contains a tissue carrier matrix comprising a plurality of biocompatible, bioresorbable granules and at least one tissue fragment in association with the granules. The tissue fragment contains one or more viable cells that can migrate from the tissue and populate the tissue carrier matrix. Also provided is a method for injectably delivering the tissue implant.

18 Claims, 6 Drawing Sheets

U.S. PATENT DOCUMENTS

| | | |
|---|---|---|
| 5,589,176 A | 12/1996 | Seare, Jr. |
| 5,595,751 A | 1/1997 | Bezwada et al. |
| 5,597,579 A | 1/1997 | Bezwada et al. |
| 5,607,687 A | 3/1997 | Bezwada et al. |
| 5,612,028 A | 3/1997 | Sackier et al. |
| 5,618,552 A | 4/1997 | Bezwada et al. |
| 5,620,698 A | 4/1997 | Bezwada et al. |
| 5,624,463 A | 4/1997 | Stone et al. |
| 5,632,745 A | 5/1997 | Schwartz |
| 5,645,850 A | 7/1997 | Bezwada et al. |
| 5,648,088 A | 7/1997 | Bezwada et al. |
| 5,654,135 A | 8/1997 | Tinois et al. |
| 5,656,492 A | 8/1997 | Glowacki et al. |
| 5,677,355 A | 10/1997 | Shalaby et al. |
| 5,681,353 A | 10/1997 | Li et al. |
| 5,697,976 A | 12/1997 | Chesterfield et al. |
| 5,698,213 A | 12/1997 | Jamiolkowski et al. |
| 5,700,583 A | 12/1997 | Jamiolkowski et al. |
| 5,709,854 A | 1/1998 | Griffith-Cima et al. |
| 5,720,969 A | 2/1998 | Gentile et al. |
| 5,723,331 A | 3/1998 | Tubo et al. |
| 5,735,903 A | 4/1998 | Li et al. |
| 5,736,372 A | 4/1998 | Vacanti et al. |
| 5,755,791 A | 5/1998 | Whitson et al. |
| 5,759,190 A | 6/1998 | Vibe-Hansen et al. |
| 5,766,631 A | 6/1998 | Arnold et al. |
| 5,769,899 A | 6/1998 | Schwartz et al. |
| 5,786,217 A | 7/1998 | Tubo et al. |
| 5,830,493 A | 11/1998 | Yokota et al. |
| 5,837,235 A | 11/1998 | Mueller et al. |
| 5,842,477 A | 12/1998 | Naughton et al. |
| 5,855,608 A | 1/1999 | Brekke et al. |
| 5,859,150 A | 1/1999 | Jamiolkowski et al. |
| 5,891,558 A | 4/1999 | Bell et al. |
| 5,902,741 A | 5/1999 | Purchio et al. |
| 5,904,716 A | 5/1999 | Gendler |
| 5,904,717 A | 5/1999 | Brekke et al. |
| 5,914,121 A | 6/1999 | Robey et al. |
| 5,922,025 A | 7/1999 | Hubbard |
| 5,964,805 A | 10/1999 | Stone |
| 5,968,096 A | 10/1999 | Whitson et al. |
| 5,980,889 A | 11/1999 | Butler et al. |
| 5,989,269 A | 11/1999 | Vibe-Hansen et al. |
| 5,990,194 A | 11/1999 | Dunn et al. |
| 5,990,378 A | 11/1999 | Ellis et al. |
| 6,001,352 A | 12/1999 | Boyan et al. |
| 6,001,394 A | 12/1999 | Daculsi et al. |
| 6,005,161 A | 12/1999 | Brekke et al. |
| 6,027,742 A | 2/2000 | Lee et al. |
| 6,042,610 A | 3/2000 | Li et al. |
| 6,054,122 A | 4/2000 | MacPhee et al. |
| 6,077,989 A | 6/2000 | Kandel et al. |
| 6,080,579 A | 6/2000 | Hanley, Jr. et al. |
| 6,096,532 A | 8/2000 | Armstrong et al. |
| 6,103,255 A | 8/2000 | Levene et al. |
| 6,110,209 A | 8/2000 | Stone |
| 6,110,212 A | 8/2000 | Gregory |
| 6,117,166 A | 9/2000 | Winston et al. |
| 6,120,514 A | 9/2000 | Vibe-Hansen et al. |
| 6,121,042 A | 9/2000 | Peterson et al. |
| 6,123,727 A | 9/2000 | Vacanti et al. |
| 6,132,463 A | 10/2000 | Lee et al. |
| 6,132,468 A | 10/2000 | Mansmann |
| 6,139,578 A | 10/2000 | Lee et al. |
| 6,140,039 A | 10/2000 | Naughton et al. |
| 6,143,293 A | 11/2000 | Weiss et al. |
| 6,153,292 A | 11/2000 | Bell et al. |
| 6,156,068 A | 12/2000 | Walter et al. |
| 6,165,217 A | 12/2000 | Hayes |
| 6,176,880 B1 | 1/2001 | Plouhar et al. |
| 6,179,840 B1 | 1/2001 | Bowman |
| 6,179,872 B1 | 1/2001 | Bell et al. |
| 6,180,007 B1 | 1/2001 | Gentile et al. |
| 6,183,737 B1 | 2/2001 | Zaleske et al. |
| 6,187,053 B1 | 2/2001 | Minuth et al. |
| 6,187,329 B1 | 2/2001 | Agrawal et al. |
| 6,197,061 B1 | 3/2001 | Masuda et al. |
| 6,197,325 B1 | 3/2001 | MacPhee et al. |
| 6,200,606 B1 | 3/2001 | Peterson et al. |
| 6,214,045 B1 | 4/2001 | Corbitt, Jr. et al. |
| 6,214,055 B1 | 4/2001 | Simionescu et al. |
| 6,242,247 B1 | 6/2001 | Rieser et al. |
| 6,251,673 B1 | 6/2001 | Winkler et al. |
| 6,277,151 B1 | 8/2001 | Lee et al. |
| 6,283,980 B1 | 9/2001 | Vibe-Hansen et al. |
| 6,287,340 B1 | 9/2001 | Altman et al. |
| 6,291,240 B1 | 9/2001 | Mansbridge et al. |
| 6,306,177 B1 | 10/2001 | Felt et al. |
| 6,306,424 B1 | 10/2001 | Vyakarnam et al. |
| 6,316,692 B1 | 11/2001 | Readhead et al. |
| 6,319,712 B1 | 11/2001 | Meenen et al. |
| 6,331,312 B1 | 12/2001 | Lee et al. |
| 6,333,029 B1 | 12/2001 | Vyakarnam et al. |
| 6,365,149 B2 | 4/2002 | Vyakarnam et al. |
| 6,378,527 B1 | 4/2002 | Hungerford et al. |
| 6,378,572 B1 | 4/2002 | Neubauer et al. |
| 6,379,367 B1 | 4/2002 | Vibe-Hansen et al. |
| 6,464,729 B1 | 10/2002 | Kandel |
| 6,485,723 B1 | 11/2002 | Badylak et al. |
| 6,489,165 B2 | 12/2002 | Bhatnagar et al. |
| 6,511,958 B1 | 1/2003 | Atkinson et al. |
| 6,521,430 B1 | 2/2003 | Orwar et al. |
| 6,530,956 B1 | 3/2003 | Mansmann |
| 6,534,084 B1 | 3/2003 | Vyakarnam et al. |
| 6,541,024 B1 | 4/2003 | Kadiyala et al. |
| 6,551,355 B1 | 4/2003 | Lewandrowski et al. |
| 6,569,172 B2 | 5/2003 | Asculai et al. |
| 6,592,588 B1 | 7/2003 | Bobic et al. |
| 6,599,323 B2 | 7/2003 | Melican et al. |
| 6,605,294 B2 | 8/2003 | Sawhney |
| 6,626,950 B2 | 9/2003 | Brown et al. |
| 6,727,224 B1 | 4/2004 | Zhang et al. |
| 6,773,458 B1 | 8/2004 | Brauker et al. |
| 6,783,712 B2 | 8/2004 | Slivka et al. |
| 6,840,962 B1 | 1/2005 | Vacanti et al. |
| 6,852,330 B2 | 2/2005 | Bowman et al. |
| 6,866,681 B2 | 3/2005 | Laboureau et al. |
| 6,884,428 B2 | 4/2005 | Binette et al. |
| 6,886,568 B2 | 5/2005 | Frondoza et al. |
| 6,886,569 B2 | 5/2005 | Chervitz et al. |
| 7,109,034 B2 | 9/2006 | Orwar et al. |
| 7,208,177 B2 | 4/2007 | Geistlich et al. |
| 7,262,020 B2 | 8/2007 | Hellerstein |
| 7,316,822 B2 | 1/2008 | Binette et al. |
| 7,368,124 B2 | 5/2008 | Chun et al. |
| 7,456,012 B2 | 11/2008 | Ryttsen et al. |
| 7,824,701 B2 | 11/2010 | Binette et al. |
| 7,875,296 B2 | 1/2011 | Binette et al. |
| 7,901,461 B2 | 3/2011 | Harmon et al. |
| 8,137,686 B2 | 3/2012 | Kladakis et al. |
| 8,137,702 B2 | 3/2012 | Binette et al. |
| 8,197,837 B2 | 6/2012 | Jamiolkowski et al. |
| 8,221,780 B2 | 7/2012 | Dhanaraj et al. |
| 8,226,715 B2 | 7/2012 | Hwang et al. |
| 2001/0014475 A1 | 8/2001 | Frondoza et al. |
| 2001/0016353 A1 | 8/2001 | Janas et al. |
| 2001/0016772 A1 | 8/2001 | Lee et al. |
| 2001/0023373 A1 | 9/2001 | Plouhar et al. |
| 2001/0038848 A1 | 11/2001 | Donda et al. |
| 2001/0039453 A1 | 11/2001 | Gresser et al. |
| 2001/0051834 A1 | 12/2001 | Frondoza et al. |
| 2001/0053353 A1 | 12/2001 | Griffith et al. |
| 2001/0053839 A1 | 12/2001 | Noishiki et al. |
| 2002/0006428 A1 | 1/2002 | Mahmood et al. |
| 2002/0009477 A1 | 1/2002 | Mahmood et al. |
| 2002/0009805 A1 | 1/2002 | Nevo et al. |
| 2002/0009806 A1 | 1/2002 | Hicks, Jr. |
| 2002/0013627 A1 | 1/2002 | Geistlich et al. |
| 2002/0015719 A1 | 2/2002 | Kellner et al. |
| 2002/0022883 A1 | 2/2002 | Burg |
| 2002/0022884 A1 | 2/2002 | Mansmann |
| 2002/0028192 A1 | 3/2002 | Dimitrijevich et al. |
| 2002/0029055 A1 | 3/2002 | Bonutti |
| 2002/0062151 A1 | 5/2002 | Altman et al. |
| 2002/0082631 A1 | 6/2002 | Bonutti |
| 2002/0083479 A1 | 6/2002 | Winston et al. |
| 2002/0091403 A1 | 7/2002 | Bonutti |

| | | | |
|---|---|---|---|
| 2002/0091406 A1 | 7/2002 | Bonutti | |
| 2002/0099401 A1 | 7/2002 | Bonutti | |
| 2002/0099448 A1 | 7/2002 | Hiles et al. | |
| 2002/0107570 A1 | 8/2002 | Sybert et al. | |
| 2002/0119177 A1 | 8/2002 | Bowman et al. | |
| 2002/0120348 A1 | 8/2002 | Melican et al. | |
| 2002/0123750 A1 | 9/2002 | Eisermann et al. | |
| 2002/0127265 A1 | 9/2002 | Bowman et al. | |
| 2002/0133229 A1 | 9/2002 | Laurencin et al. | |
| 2002/0133235 A1 | 9/2002 | Hungerford et al. | |
| 2002/0150604 A1 | 10/2002 | Yi et al. | |
| 2002/0151975 A1 | 10/2002 | Farr et al. | |
| 2002/0173558 A1 | 11/2002 | Williams et al. | |
| 2002/0176893 A1 | 11/2002 | Wironen et al. | |
| 2002/0177224 A1 | 11/2002 | Madry et al. | |
| 2003/0003153 A1 | 1/2003 | Asculai et al. | |
| 2003/0004578 A1 | 1/2003 | Brown et al. | |
| 2003/0012805 A1 | 1/2003 | Chen et al. | |
| 2003/0023316 A1 | 1/2003 | Brown et al. | |
| 2003/0026787 A1 | 2/2003 | Fearnot et al. | |
| 2003/0027332 A1 | 2/2003 | Lafrance et al. | |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0036801 A1 | 2/2003 | Schwartz et al. | |
| 2003/0050709 A1 | 3/2003 | Noth et al. | |
| 2003/0064917 A1 | 4/2003 | Crawford et al. | |
| 2003/0075822 A1 | 4/2003 | Slivka et al. | |
| 2003/0077311 A1 | 4/2003 | Vyakarnam et al. | |
| 2003/0078617 A1 | 4/2003 | Schwartz et al. | |
| 2003/0147935 A1 | 8/2003 | Binette et al. | |
| 2003/0193104 A1 | 10/2003 | Melican et al. | |
| 2004/0024457 A1 | 2/2004 | Boyce et al. | |
| 2004/0059416 A1 | 3/2004 | Murray et al. | |
| 2004/0078077 A1 | 4/2004 | Binette et al. | |
| 2004/0078090 A1 | 4/2004 | Binette et al. | |
| 2004/0219182 A1 | 11/2004 | Gomes et al. | |
| 2004/0236424 A1 | 11/2004 | Berez et al. | |
| 2004/0267362 A1 | 12/2004 | Hwang et al. | |
| 2005/0002915 A1 | 1/2005 | Atala et al. | |
| 2005/0038520 A1 | 2/2005 | Binette et al. | |
| 2005/0048651 A1 | 3/2005 | Ryttsen et al. | |
| 2005/0113937 A1 | 5/2005 | Binette et al. | |
| 2005/0125077 A1 | 6/2005 | Harmon et al. | |
| 2005/0147645 A1 | 7/2005 | Budny | |
| 2005/0177249 A1 | 8/2005 | Kladakis et al. | |
| 2005/0232967 A1 | 10/2005 | Kladakis et al. | |
| 2005/0234549 A1 | 10/2005 | Kladakis et al. | |
| 2006/0067967 A1 | 3/2006 | Bowman et al. | |
| 2006/0084930 A1 | 4/2006 | Dhanaraj et al. | |
| 2006/0204439 A1 | 9/2006 | Hellerstein | |
| 2006/0223177 A1 | 10/2006 | Harris et al. | |
| 2006/0280768 A1 | 12/2006 | Hwang et al. | |
| 2006/0293760 A1 | 12/2006 | DeDeyne | |
| 2007/0031470 A1 | 2/2007 | Kladakis et al. | |
| 2007/0036767 A1 | 2/2007 | Mistry et al. | |
| 2007/0250177 A1 | 10/2007 | Bilbo | |
| 2008/0039955 A1 | 2/2008 | Hunziker | |
| 2008/0071385 A1 | 3/2008 | Binette et al. | |
| 2008/0226870 A1 | 9/2008 | Sypeck et al. | |
| 2011/0009963 A1 | 1/2011 | Binnette et al. | |
| 2011/0091517 A1 | 4/2011 | Binette et al. | |
| 2011/0097381 A1 | 4/2011 | Binette et al. | |
| 2011/0110958 A1 | 5/2011 | Qiu et al. | |
| 2011/0177134 A1 | 7/2011 | Harmon et al. | |
| 2012/0165939 A1 | 6/2012 | Kladakis et al. | |

FOREIGN PATENT DOCUMENTS

| | | | |
|---|---|---|---|
| DE | 19812195 A1 | 9/1999 | |
| EP | 0145492 A2 | 6/1985 | |
| EP | 0274898 A2 | 7/1988 | |
| EP | 0277678 A1 | 8/1988 | |
| EP | 0464163 A1 | 1/1992 | |
| EP | 0 562 864 | 9/1993 | |
| EP | 0 955 024 | 11/1999 | |
| EP | 1027897 A1 | 8/2000 | |
| EP | 1 064 958 | 1/2001 | |
| EP | 1 167 517 | 1/2002 | |
| EP | 1177800 A1 | 2/2002 | |
| EP | 1 216 718 A | 6/2002 | |
| EP | 1348451 A1 | 10/2003 | |
| EP | 1 405 649 A1 | 4/2004 | |
| EP | 1410811 A1 | 4/2004 | |
| EP | 1506790 A1 | 2/2005 | |
| EP | 1537839 A1 | 6/2005 | |
| EP | 1 604 622 | 12/2005 | |
| FR | 2688690 A1 | 9/1993 | |
| GB | 1008193 A | 10/1965 | |
| JP | 02-052648 A | 2/1990 | |
| JP | 2143945 A | 6/1990 | |
| JP | 02-227442 A | 9/1990 | |
| JP | 02-256824 A | 10/1990 | |
| JP | 03-261753 A | 11/1991 | |
| JP | 04-094329 A | 3/1992 | |
| JP | 10-129048 A | 5/1998 | |
| JP | 10234844 A | 9/1998 | |
| JP | 10-319783 A | 12/1998 | |
| JP | 11-319068 A | 11/1999 | |
| JP | 2001129073 A | 5/2001 | |
| JP | 2002-527402 A | 8/2002 | |
| JP | 2002-535378 A | 10/2002 | |
| JP | 2003320008 A | 11/2003 | |
| JP | 2004008437 A | 1/2004 | |
| JP | 20020165345 A | 1/2004 | |
| JP | 2004-195103 A | 7/2004 | |
| JP | 2005-237476 A | 9/2005 | |
| RU | 2187261 C1 | 8/2002 | |
| SU | 1535542 A1 | 1/1990 | |
| WO | WO-86/00533 | 1/1986 | |
| WO | WO-9206179 A1 | 4/1992 | |
| WO | WO-93/02718 A1 | 2/1993 | |
| WO | WO-93/11805 A1 | 6/1993 | |
| WO | WO-95/33821 | 12/1995 | |
| WO | WO-96/08277 A1 | 3/1996 | |
| WO | WO-97/30662 | 8/1997 | |
| WO | WO-97/46665 | 12/1997 | |
| WO | WO-98/48860 | 11/1998 | |
| WO | WO-9853768 A1 | 11/1998 | |
| WO | WO-9905992 A1 | 2/1999 | |
| WO | WO-99/16381 | 4/1999 | |
| WO | WO-9939724 A1 | 8/1999 | |
| WO | WO-99/47097 | 9/1999 | |
| WO | WO-9959647 A1 | 11/1999 | |
| WO | WO-00/15248 A2 | 3/2000 | |
| WO | WO-00/16381 A1 | 3/2000 | |
| WO | WO-00/69355 A1 | 11/2000 | |
| WO | WO-00/72782 A1 | 12/2000 | |
| WO | WO-00/74741 A2 | 12/2000 | |
| WO | WO-01/15753 A1 | 3/2001 | |
| WO | WO-01/34065 A1 | 5/2001 | |
| WO | WO-01/85226 A1 | 11/2001 | |
| WO | WO-02/00272 A2 | 1/2002 | |
| WO | WO-02/05750 A2 | 1/2002 | |
| WO | WO-02/30324 A1 | 4/2002 | |
| WO | WO-02062357 A1 | 8/2002 | |
| WO | WO-02/074356 A1 | 9/2002 | |
| WO | WO-02/096268 A2 | 12/2002 | |
| WO | WO-03/007789 A2 | 1/2003 | |
| WO | WO-03/017826 A2 | 3/2003 | |
| WO | WO-03043674 A1 | 5/2003 | |
| WO | WO-2004012782 A1 | 2/2004 | |

OTHER PUBLICATIONS

Australian Search Report for AU application No. 2006200194, mailed Feb. 4, 2008.
Boland et. al., J. Macromol. Sci.-Pure Appl. Chem., 2001, A38(12), p. 1231-1243).
Bonisch, M., et al. "Septumredonstrucktion mit PDS-Folie" HNO 47: 1999 pp. 546-550.
Buschmann et al., J. Orthop. Res. 1992; 10:745-752.
Caterson EJ., et al. "Three-Dimensional Cartilage Formation by Bone Marrow-Derived Cells Seeded in Polylactide/Alginate Amalgam," *J Biomed Mater Res.* 57(3):394-403 (2001) (Abstract Only).
Chen G., Ushida T. and Tateishi T. "A hybrid network of synthetic polymer mesh and collagen sponge," Chem. Commun., 2000, 1505-1506.

De Groot, J.H. et al., "Meniscal tissue regeneration in porous 50/50 copoly(l-lactide/epsilon-caprolactone) implants" Biomaterials, vol. 18, No. 8, 1997, pp. 613-622.

De Groot, J.H. et al., "Use of porous polyurethanes for meniscal reconstruction and meniscal prostheses" Biomaterials, vol. 17, No. 2, 1996, pp. 163-173.

Defrere et al., "Teflon/polyurethane arthroplasty of the knee: the first 2 years preliminary clinical experience in a new concept of artificial resurfacing of full thickness cartilage legions of the knee," Acta Chir. Belg., 1992, vol. 92, No. 5, pp. 217-227.

Deuel, T. et al., "Growth Factors in Principles of Tissue Engineering," Second Edition, Academic Press pp. 129-141 (2000).

Dialog English language abstract for DE 19812195, published Sep. 30, 1999.

Eckersberger, M.D., Franz, "Circumferential tracheal replacement with costal cartilage", The Journal of Thoracic and Cardiovascular Surgery, 1987;94: pp. 175-180.

European Search Report for EP 08075114.2, mailed May 12, 2010.
European Search Report for EP 10075307 mailed Oct. 6, 2010.
European Search Report, for EP 03 25 6522, mailed Feb. 24, 2004.
European Search Report, for EP Application No. 07252617.1, mailed Nov. 2, 2007.

Examination file history of EP 01310810, priority date of Dec. 21, 2000.

Frenkel, S, Ph.D. and Paul E. Di Cesare, M.D., "Degradation and Repair of Articular Cartilage," Frontiers in Bioscience, 4$^{th}$ ed., pp. 671-685, pp. 1-32 (Oct. 15, 1999).

Gooch, K. et al., "Mechanical Forces and Growth Factors Utilized in Tissue Engineering" Frontier in Tissue Engineering, Pergamon Chapter II.3, pp. 61-82 (1998).

Grigolo, B., et al. "Transplantation of Chondrocytes Seeded on a Hyaluronan Derivative (hyaff-11) into Cartilage Defects in Rabbits," Biomaterials 22(17):2417-2424 (2001) (Abstract Only).

Heller: 'Handbook of Biodegradable Polymers', 1997, Hardwood Academic Press pp. 99-118.

Hutmacher DW., "Scaffold Design and Fabrication Technologies for Engineering Tissues-State of the Art and Future Prospectives", J Biomater Sci Polym Ed, 12(1):107-124 (2001) (Abstract Only).

Hutmacher DW., "Scaffolds in Tissue Engineering Bone and Cartilage", Biomaterials, 21(24):2529-2543 (2000) (Abstract Only).

Ibarra, C. M.D. et al. "Tissue-Engineered Meniscus—Cells and Matrix", Tissue Engineering in Orthopedic Surgery 31(3):411-418 (Jul. 2000).

Ikada, Yoshito, Handbook of Fiber Science and Technology, Edited by Menachem Lewin, Jack Preston, vol. III, Part B, Chapter 8, pp. 253, 289-295, Published by M. Dekker, 1983.

Japanese Office Action, from JP 2004-191861, mailed Mar. 1, 2011.

Journal of Biomaterials Research, vol. 22, pp. 993-1009, 1988 by Cohn and Younes.

Kemnitzer and Kohn, in the Handbook of Biodegradable Polymers, edited by Domb, et. al., Hardwood Academic Press, pp. 251-272 (1997).

Koski, J. M.D. et al., "Meniscal Injury and Repair", Orthopedic Clinics of North American, 31(3):419-435 (Jul. 2000).

Koski, J. M.D. et al., "Tissue-Engineered Ligament—Cells, Matrix, and Growth Factors" Tissue Engineering in Orthopedic Surgery, 31(3):437-452 (Jul. 2000).

Kurashina, K. et al. "Osteogenesis in muscle with composite graft of hydroxyapatite and autogenous calvarial periosteum: a preliminary report" Biomaterials (1995) vol. 16, No. 2, pp. 119-123.

Matsuo, M.D., Kiyoshi et al., "Semiquantitative Correction of Post-traumatic Enophthalmos with Sliced Cartilage Grafts" Plastic and Reconstructive Surgery, vol. 83, No. 3, Postraumatic Enophthalmos, pp. 429-437 (1989).

Megumi, M.D., Yoshikazu, "Augmentation Rhinoplasty with Soft Tissue and Cartilage" Aesthetic Plastic Surgery, 1988, pp. 89-93.

Microcellular Foams via Phase Separation, J. Vac. Sci. Technolol., A.T. Young, vol. 4(3), May/Jun. 1986.

Murray, M., et al. "The Migration of Cells from the Ruptured Human Anterior Cruciate Ligament into Collagen-Glycosaminoglycan Regeneration Templates in Vitro," Biomaterials 22:2393-2402 (2001).

Noishiki Y., "A new trend in hybrid artificial organs" J. Artificial Organs, 1999, vol. 2: pp. 93-96.

Papadopulos, M.D., Angel, "Compound Implant to Project the Nasal Tip" Aesthetic Plastic Surgery, 1987, pp. 181-185.

Partial European Search Report, for EP 04 25 7515, mailed May 9, 2005.

Polymer Preprints (ACS Division of Polymer Chemistry), vol. 30(1), p. 498, 1989 by Cohn.

Powers, Dennis L. et al., "A cartilagenous graft as an adjunct to finger joint implant arthroplasty" Journal of Biomedical Materials Research, vol. 19, 1985 pp. 509-518.

Radice, M. "Hyaluronan-Based Biopolymers as delivery vehicles for Bone-Marrow-Derived Mesenchymal Progenitors", J Biomed Mater Res. 50(2):101-9 (2000) (Abstract Only).

Rohrbach, Jens Martin et al., "Biological Corneal Replacement—Alternative to Keratoplasty and Keratoprosthesis? A Pilot Study with Heterologous Hyaline Cartilage in the Rabbit Model", Klin Monatsbl Augenheilkd 207, 1995; pp. 191-196.

Rossi, et al., "Embryonic Purkinje Cells Grafted on the Surface of the Cerebellar Cortex Integrate in the Adult Unlesioned Cerebellum," EP J. Neuroscience 4:589-93 (1992).

Sampath, T. K., et al. "In Vitro Transformation of Mesenchymal Cells Derived From Embryonic Muscle Into Cartilage in Response to Extracellular Matrix Components of Bone," Proceedings of the National Academy of Science of the USA, 81(1): 3419-3423 (Jun. 1984).

Schreiber RE., et al. "A Method for Tissue Engineering of cartilage by Cell Seeding on Bioresorbable Scaffolds," Ann NY Acad Sci. 875:394-404 (1999) (Abstract Only).

Solov'ev et al., "Functional Activity of Hepatocytes in Liver Fragments in Vitro as a Function if Fragment Size and Duration of Culturing" Bull Exp Biol Med. Jun. 2000;129(6):595-7.

Spaans et al. "Solvent-free fabrication of micro-porous polyurethane amide and polyurethaneurea scaffolds for repair and replacement of the knee joint meniscus" Journal of Biomaterials, vol. 21, No. 23, 2000, pp. 2453-2460.

Stone, K. et al. "Meniscal Regeneration with Copolymeric Collagen Scaffolds," American Journal of Sports Medicine 20(2):104-111 (1992).

Tienen T. G. et al., "A porous polymer scaffold for meniscal lesion repair-A study in dogs" Biomaterials, vol. 24, No. 14, 2003, pp. 2541-2548.

Tozum et al., J Canadian Dental Assoc. Nov. 2003 69(10):664-664h.

Trenite, M.D., G.J. Nolst et al.., "Reimplantation of autologous septal cartilage in the growing nasal septum", Rhinology, 25, 1987, pp. 225-236.

van Susante JLC, et al. "Linkage of Chondroitin-Sulfate to Type I Collagen Scaffolds Stimulates the Bioactivity of Seeded Chondrocytes in Vitro", Biomaterials 22(17):2359-2369 (2001) (Abstract Only).

Vandorpe, et al in the Handbook of Biodegradable Polymers, edited by Domb, et al., Hardwood Academic Press, pp. 161-182 (1997).

www.bio-medicine.org/medicine-technology-1/New-Study-Shows-Cloning-From-Dried-Cells-Now-Possible-2988-1/, 2 pgs, printed Jan. 11, 2010.

www.btc-bti.com/applications/cryogenicstorage.htm, 6 pgs, printed Jan. 11, 2010.

Japanese Office Action issued Aug. 28, 2012 for Application No. 2004-233655 (6 Pages).

Takeuchi et al., The present situation and vision of joint transplantation. Journal of Clinical and Experimental Medicine. 1995; 164(10):748-9. Translation.

Japanese Office Action issued Feb. 26, 2013 for Application No. 2007-171032 (4 Pages).

CONFORMABLE TISSUE REPAIR IMPLANT CAPABLE OF INJECTION DELIVERY

The present invention is a continuation of U.S. patent application Ser. No. 12/980,544, filed on Dec. 29, 2010, entitled "Conformable Tissue Repair Implant Capable of Injection Delivery," now U.S. Pat. No. 8,137,702, and a continuation of U.S. patent application Ser. No. 11/947,384, filed on Nov. 29, 2007, entitled "Conformable Tissue Repair Implant Capable of Injection Delivery," now U.S. Pat. No. 7,875,296, and a continuation of U.S. patent application Ser. No. 10/723,982, filed on Nov. 26, 2003, entitled "Conformable Tissue Repair Implant Capable of Injection Delivery," now U.S. Pat. No. 7,316,822. The entire contents of these applications are incorporated herein by reference.

STATEMENT REGARDING FEDERALLY SPONSORED RESEARCH

Not applicable.

FIELD OF THE INVENTION

The present invention relates to methods and apparatus for the treatment of tissue injuries or defects. Specifically, the present invention relates to tissue repair and augmentation implants, and more particularly, to a conformable tissue repair and augmentation implant capable of injection and a method for its minimally invasive delivery.

BACKGROUND OF THE INVENTION

Injuries to soft tissue, such as cartilage, skin, muscle, bone, tendon and ligament, where the tissue has been injured or traumatized frequently require surgical intervention to repair the damage and facilitate healing. Such surgical repairs can include suturing or otherwise repairing the damaged tissue with known medical devices, augmenting the damaged tissue with other tissue, using an implant, a graft or any combination of these techniques. Despite these conventional methods of tissue repair, there is a continuing need in this art for novel surgical techniques for the surgical treatment of damaged tissue (e.g., cartilage, meniscal cartilage, ligaments, tendons and skin) that can effect a more reliable tissue repair over the long term and can facilitate the healing of injured tissue.

Recently, tissue engineering approaches to repairing tissue damage or injury have been used with increasing frequency. These methods typically involve replacing or reconstructing damaged or injured tissue with cells capable of new tissue growth. The cells are usually incorporated into a delivery vehicle such as a surgical implant for placement at the tissue site, whereupon the healthy cells can grow into their surrounding environment. Various surgical implants are known and have been used in surgical procedures to help achieve these benefits. For example, it is known to use various devices and techniques for creating implants having isolated cells loaded onto a delivery vehicle. Such cell-seeded implants are used in an in vitro method of making and/or repairing cartilage by growing cartilaginous structures that consist of chondrocytes seeded onto biodegradable, biocompatible fibrous polymeric matrices. Such methods require the initial isolation of chondrocytes from cartilaginous tissue prior to the chondrocytes being seeded onto the polymeric matrices. Other techniques for repairing damaged tissue employ implants having stem or progenitor cells that are used to produce the desired tissue. For example, it is known to use stem or progenitor cells, such as the cells within fatty tissue, muscle, or bone marrow, to regenerate bone and/or cartilage in animal models. The stem cells are removed from the animal and placed in an environment favorable to cartilage formation, thereby inducing the fatty tissue cells to proliferate and to create a different type of cell, such as cartilage cells.

While the trend towards using tissue engineering approaches to tissue repair continues to gain popularity, mainly because of the long-term benefits provided to the patient, these current techniques are not without drawbacks. One disadvantage with current tissue engineering techniques is that they can be time consuming. A typical process involves the harvest of cellular tissue in a first surgical procedure, which is then transported to a laboratory for cell culturing and amplification. The tissue sample is treated with enzymes that will release the cells from the matrix, and the isolated cells will be grown for a period of 3 to 4 weeks using standard cell culture techniques. Once the cell population has reached a target number, the cells are sent back to the surgeon for implantation during a second surgical procedure. This manual labor-intense process is extremely costly and time consuming. Although the clinical data suggest long term benefits for the patient, the prohibitive cost of the procedure combined with the traumatic impact of two surgical procedures, has hampered adoption of this technique.

The current model for tissue repair generally involves retrieving a cell sample from a patient, isolating the cells, culturing the cells for several weeks, and then implanting them in a defect, either with or without a scaffold. Preferably, a scaffold is used in order to facilitate newly developing cell growth. In the past, such scaffolds have consisted mostly of two- or three-dimensional porous scaffolds that allow cell invasion and remodeling once the scaffold has been combined with living cells and has been delivered inside the patient. This model is limited in application because of the secondary surgery and high costs involved. More importantly, one limitation of using such scaffolds is that tissue defect geometry can often be unpredictable. Since the scaffold geometry is essentially limited to what has been manufactured, the scaffold carrier to be implanted rarely matches perfectly the site. In order to achieve a desirable complementary fit with the defect or injury site, the scaffold often needs to be revised by trimming prior to or after implantation. This additional adjustment time adds onto the overall surgery time for the patient. For certain difficult to match or unusually shaped sites, even the step of trimming the scaffold does not ensure an ideal fit with the implantation site. Further, where relatively large tissue defects are involved, minimally invasive surgery may not be possible due to the limited size of the surgical access site. Therefore, delivery of large scaffolds may require an open procedure which poses more risks to the patient.

Injectable gels and microcarrier beads have also been used in the past as cell delivery vehicles. These systems have the advantage of sometimes being injectable and therefore require less invasive procedures for implantation. Typically, these carriers have been combined with isolated cells, which are sensitive to manipulation such as shear, or the presence of crosslinkers that are required to allow the carrier to be fixed or set in place. Hence, these systems have proven to be less than ideal due to the problems associated with cell viability once incorporated into these carrier systems. Accordingly, there continues to exist a need in this art for a method of delivering tissue repair implants through a minimally invasive procedure. Also desirable is a conformable tissue repair or augmentation implant that can adapt to the shape or geometry of the tissue site. The implant should be suitable for delivering viable tissue capable of effecting new cell growth. It is also desirable to provide a method for making such an implant, whereby the implant can be made in a quick and efficient manner for immediate use during surgery.

SUMMARY OF THE INVENTION

This invention relates to a conformable tissue implant for use in treating injured or defective tissue, and a method for delivering such an implant in a minimally invasive procedure. The implant is configured to be introduced to the tissue site, where it can assume the shape or geometry of the tissue defect or injury site, thereby providing a close interface between the implant and the tissue site which enhances healing and promotes new cellular growth to occur. The biocompatible tissue implant can be used for the repair, augmentation and/or regeneration of diseased or damaged tissue. Further, the tissue implant can be used for tissue bulking, cosmetic treatments, therapeutic treatments, tissue augmentation, as well as tissue repair.

The tissue repair implant of the present invention comprises finely minced tissue fragments combined with a tissue carrier matrix formed of biocompatible, bioresorbable granules. The tissue fragments can be derived from a number of sources, including connective tissue such as cartilage, meniscus, tendon, ligament, dermis, bone, or combinations thereof. In addition, the tissue fragments can be autogenic tissue, allogeneic tissue, xenogeneic tissue, or combinations thereof. The tissue fragments serve as a cell source for new cellular growth, and have an effective amount of viable cells that can migrate out of the tissue fragment and populate the tissue carrier matrix once the implant is delivered to the patient. The granules serve as a microcarrier to provide sufficient mechanical integrity for cellular integration with the surrounding environment during the tissue remodeling process. In one aspect of the present invention, the finely minced tissue fragments and granules together form an injectable suspension that can be delivered by injection in a minimally invasive procedure. Over time, the plurality of biocompatible, bioresorbable granules are resorbed to leave behind the new tissue at the implant site.

In one embodiment of the present invention, the tissue carrier matrix further includes a binding agent that acts to gel together or facilitate cohesion of the tissue fragments and granules within the tissue carrier matrix. The binding agent enables the implant to take on a semi-solid or gel-like form. Where a solid or cured implant is desired, a curing agent can additionally be provided with the tissue carrier matrix. This curing agent would act to crosslink the binding agent, thereby forming a solid implant within which are the tissue fragments and the bioresorbable, biocompatible granules. In one aspect, the implant is cured once it is delivered to the implantation site. In another aspect, the implant is cured prior to its delivery to the implantation site. To further enhance the implant's regenerative or reconstructive abilities, the tissue carrier matrix can also include a biological component or effector which enhances the effectiveness of the tissue fragments to new cellular growth.

The invention also provides to a method of repairing a tissue defect or injury which involves the steps of providing a tissue repair implant in accordance with the present invention and delivering the tissue repair implant to a tissue defect or injury site. In one aspect, the step of delivering includes injecting the tissue repair implant into the tissue defect site. The tissue carrier matrix can also include a curing agent, and the method of the present invention can further include the step of allowing the tissue repair implant to set at the tissue defect site. Alternatively, the tissue repair implant can be allowed to set prior to delivering the tissue repair implant to the tissue defect or injury site. At least one tissue fragment associated with the tissue carrier matrix comprises a type that is the same as the tissue to be treated. However, the tissue fragment can also comprise a type that is different from the tissue to be treated.

The invention also provides a method of preparing a tissue repair implant in accordance with the present invention, which involves the steps of providing a tissue carrier matrix comprising a plurality of biocompatible, bioresorbable granules, introducing a fluid suspension containing at least one tissue fragment to the tissue carrier matrix, the tissue fragment having an effective amount of viable cells capable of migrating out of the tissue fragment and into the tissue carrier matrix, separating the at least one tissue fragment from the fluid suspension, and collecting the tissue carrier matrix with the at least one tissue fragment for implantation at a tissue site to be repaired. The tissue carrier matrix can be provided with a binding agent which enables the implant to form a gel-like or semi-solid implant. A curing agent can additionally be provided to enable the implant to set either before or after delivery to the implantation site. A biological component or an effector can also be added to the tissue carrier matrix to further enhance the effectiveness of the tissue fragments.

The tissue implant of the present invention aims to accomplish several tasks simultaneously in order to provide more efficient delivery of a tissue repair implant to a site of tissue injury or defect. The invention combines the utility of sieving or capturing a biological agent in a carrier, with the advantage of being able to immediately use the biological agent in an intraoperative procedure, in order to deliver a conformable tissue implant loaded with tissue fragments containing living cells to a tissue implantation site. Another advantage provided by the tissue repair implant of the present invention is that there is no need to isolate cells, nor is there a need to grow tissue or attach cells to the carrier prior to delivering the implant to the implantation site. Also, by using a carrier comprising bioabsorbable, biocompatible granules, the implant is able to combine sustained drug delivery capabilities and structural integrity provided by a scaffold support with the convenience of injection delivery.

In embodiments in which the implant is used for tissue repair, the tissue repair implant can be used to treat a variety of injuries, such as injuries occurring within the musculoskeletal system (e.g., rotator cuff injuries, ACL ruptures, and meniscal tears), as well as injuries occurring in other connective tissues, such as skin and cartilage. Furthermore, such implants can be used in other orthopaedic surgical procedures, such as hand and foot surgery, to repair tissues such as ligaments, nerves, and tendons.

DETAILED DESCRIPTION OF THE INVENTION

In general, the invention relates to a tissue repair implant that comprises finely minced tissue fragments combined with a tissue carrier matrix formed of a plurality of granules. The tissue fragments serve as a cell source for new cellular growth, and the tissue fragments have an effective amount of viable cells that can migrate out of the tissue fragment to populate the tissue carrier matrix once the implant is delivered to the patient. The granules serve as a microcarrier to provide sufficient mechanical integrity for cellular integration with the surrounding environment during the tissue remodeling process. In one aspect of the present invention, the finely minced tissue fragments and granules together form an injectable suspension that can be delivered by injection to a target site in a minimally invasive procedure. By providing the implant in a suspension form, the implant is able to conform to any defect size, shape or geometry, and can assume a shape complementary to that of the implantation site. Ultimately, this feature of the invention provides an implant having a close interface with the tissue area to be repaired, thereby enhancing tissue remodeling and healing.

The biocompatible tissue implants of the present invention are used in the treatment of various types of tissue for various purposes. For example, the implants can be used for the remodeling, repair and/or regeneration of diseased or damaged tissue. Although the implants are sometimes referred to herein as "tissue repair implants" and the methods of using the implants are sometimes characterized as tissue repair techniques, it is understood that the implants can be used for a variety of tissue treatments, including but not limited to tissue remodeling, tissue repair, tissue bulking, tissue augmentation, cosmetic treatments, therapeutic treatments, and for tissue sealing.

The tissue repair implant includes at least one sample of viable tissue that is associated with at least a portion of the tissue carrier matrix. The term "viable," as used herein, refers to a tissue sample having one or more viable cells. Virtually any type of tissue can be used to construct the tissue repair implants of the present invention. For example, the tissue used can be obtained from a connective tissue such as cartilage tissue, meniscal tissue, ligament tissue, tendon tissue, skin tissue, bone tissue, muscle tissue, periosteal tissue, pericardial tissue, synovial tissue, nerve tissue, fat tissue, kidney tissue, bone marrow, liver tissue, bladder tissue, pancreas tissue, spleen tissue, intervertebral disc tissue, embryonic tissue, periodontal tissue, vascular tissue, blood and combinations thereof. In one embodiment useful for cartilage repair, the tissue is free of bone tissue and is selected from the group consisting of fibrocartilage tissue containing chondrocytes, meniscal tissue, ligament tissue and tendon tissue. The tissue used to construct the tissue implant can be autogenic tissue, allogeneic tissue, or xenogeneic tissue. For example, healthy cartilage tissue, bone marrow tissue or aspirates are suitable for use with tissue repair implants for repairing condylar surfaces. It is also contemplated that the tissue to be used can be of the same type or a different type than the tissue to be treated with the implant.

In one embodiment useful for meniscal repair, the tissue used in the tissue repair implant can be selected from the group consisting of meniscal tissue, cartilage tissue, skin, synovial tissue, periosteal tissue, pericardial tissue, fat tissue, bone marrow, blood, tendon tissue, ligament tissue, or combinations thereof. The tissue can be obtained using any of a variety of conventional techniques, such as for example, by biopsy or other surgical removal. Preferably, the tissue sample is obtained under aseptic conditions. Once a sample of living tissue has been obtained, the sample can then be processed under sterile conditions to create a suspension having at least one minced, or finely divided, tissue particle. The particle size of each tissue fragment can vary, for example, the tissue size can be in the range of about 0.1 to about 3 mm$^3$, in the range of about 0.5 to about 1 mm$^3$, in the range of about 1 to about 2 mm$^3$, or in the range of about 2 to about 3 mm$^3$, but preferably the tissue particle is less than about 1 mm$^3$.

Preferably, the minced tissue fragment has at least one viable cell that can migrate from the tissue fragment into the tissue carrier matrix. More preferably, the tissue contains an effective amount of cells that can migrate from the tissue fragment and begin populating the tissue carrier matrix of granules after implantation. In an optional embodiment, the minced tissue fragments may be contacted with a matrix-digesting enzyme to facilitate cell migration out of the extracellular matrix surrounding the cells. The enzymes are used to increase the rate of cell migration out of the extracellular matrix and into the tissue carrier matrix. Suitable digesting enzymes that can be used in the present invention include, but are not limited to, collagenase, metalloproteinase, chondroitinase, trypsin, elastase, hyaluronidase, peptidase, dispase, thermolysin and protease.

In one embodiment, the minced tissue particles can be formed as a suspension in which the tissue particles are associated with a physiological buffering solution. Suitable physiological buffering solutions include, but are not limited to, saline, phosphate buffer solution, Hank's balanced salts, Tris buffered saline, Hepes buffered saline and combinations thereof. In addition, the tissue can be minced in any standard cell culture medium known to those skilled in the art, either in the presence or absence of serum. Prior to combining the minced tissue fragments with the granules of the tissue carrier matrix, the minced tissue suspension can be filtered and concentrated, such that only a small quantity of physiological buffering solution remains in the suspension to prevent the tissue particles from drying out. Preferably, the minced tissue fragments in solution are at concentration in the range of approximately 1 to about 100 mg/cm$^2$, and more preferably in the range of about 1 to about 20 mg/cm$^2$.

The tissue samples used in the present invention are obtained from a donor (autogenic, allogeneic, or xenogeneic) using appropriate harvesting tools. The tissue samples can be finely minced and divided into small particles either as the tissue is collected, or alternatively, the tissue sample can be minced after it is harvested and collected outside the body. In embodiments where the tissue sample is minced after it is harvested, the tissue samples can be weighed and then washed three times in phosphate buffered saline. Approximately 300 to 500 mg of tissue can then be minced in the presence of a small quantity, such as, for example, about 1 ml, of a physiological buffering solution, such as, for example, phosphate buffered saline, or a matrix digesting enzyme, such as, for example, 0.2% collagenase in Hams F12. The mincing action divides the tissue sample into particles or small pieces of approximately 1 mm$^3$. Mincing the tissue can be accomplished by a variety of methods. In one embodiment, the mincing is accomplished with two sterile scalpels using a parallel direction, and in another embodiment, the tissue can be minced by a processing tool that automatically divides the tissue into particles of a desired size. In another embodiment, the minced tissue can be separated from the physiological fluid and concentrated using any of a variety of methods known to those having ordinary skill in the art, such as for example, sieving, sedimenting or centrifuging with the bed of granules. In embodiments where the minced tissue is filtered and concentrated, the suspension of minced tissue preferably retains a small quantity of fluid in the suspension to prevent the tissue from drying out.

In the present invention, the minced tissue fragments are combined with a tissue carrier matrix formed of a plurality of granules. Preferably, the granules are formed from a bioresorbable or bioabsorbable material that has the ability to resorb in a timely fashion in the body. Over time, the biocompatible, bioresorbable granules are resorbed to leave behind the new tissue at the implant site. The granules can be formed from a variety of biocompatible, bioresorbable materials. For example, the granules can be formed from aliphatic polyesters, copoly(ether-esters), solid copolymers of fatty acid esters of glycerol and succinic acid, polyoxaesters, collagen, gelatin, albumin, hyaluronate, glucosaminoglycans, polyanhydrides, polyphosphazines, subintestinal mucosa, acellular tissues, and combinations thereof. In addition, the granules can be porous and/or have surface features such as roughness or texture. Such features would further enhance the effectiveness of the granules to attach and combine with the minced tissue fragments as well as to the tissue implant site.

Suitable aliphatic polyesters include homopolymers or copolymers of lactides, glycolides, ε-caprolactone, p-dioxanone (1,4-dioxan-2-one), trimethylene carbonate (1,3-dioxan-2-one), and combinations thereof. One skilled in the art will appreciate that the differences in the absorption time under in vivo conditions can be the basis for combining two different polymers to form the granules of the present invention. For example, a copolymer of 35:65 ε-caprolactone and glycolide (a relatively fast absorbing polymer) can be blended with 40:60 ε-caprolactone and L-lactide copolymer (a relatively slow absorbing polymer) to form a suitable tissue carrier matrix.

Other useful polymers include polyphosphazenes, co-, ter- and higher order mixed monomer based polymers made from L-lactide, D,L-lactide, lactic acid, glycolide, glycolic acid, para-dioxanone, trimethylene carbonate and εε-caprolactone such as are described by Allcock in The Encyclopedia of Polymer Science, Vol. 13, pages 31-41, Wiley Intersciences, John Wiley & Sons, 1988 and by Vandorpe, et al in the Handbook of Biodegradable Polymers, edited by Domb, et al., Hardwood Academic Press, pp. 161-182 (1997).

As used herein, the term "glycolide" is understood to include polyglycolic acid. Further, the term "lactide" is understood to include L-lactide, D-lactide, blends thereof, and lactic acid polymers and copolymers.

Elastomeric copolymers are also particularly useful in the present invention. Suitable elastomeric polymers include those with an inherent viscosity in the range of about 1.2 dL/g to 4 dL/g, more preferably about 1.2 dL/g to 2 dL/g and most preferably about 1.4 dL/g to 2 dL/g as determined at 25° C. in a 0.1 gram per deciliter (g/dL) solution of polymer in hexafluoroisopropanol (HFIP). Further, suitable elastomers exhibit a high percent elongation and a low modulus, while possessing good tensile strength and good recovery characteristics. In the preferred embodiments of this invention, the elastomer exhibits a percent elongation greater than about 200 percent and preferably greater than about 500 percent. In addition to these elongation and modulus properties, suitable elastomers should also have a tensile strength greater than about 500 psi, preferably greater than about 1,000 psi, and a tear strength of greater than about 50 lbs/inch, preferably greater than about 80 lbs/inch.

Exemplary biocompatible elastomers that can be used in the present invention include, but are not limited to, elastomeric copolymers of ε-caprolactone and glycolide (including polyglycolic acid) with a mole ratio of ε-caprolactone to glycolide of from about 35:65 to about 65:35, more preferably from 45:55 to 35:65; elastomeric copolymers of ε-caprolactone and lactide (including L-lactide, D-lactide, blends thereof, and lactic acid polymers and copolymers) where the mole ratio of ε-caprolactone to lactide is from about 35:65 to about 65:35 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of ε-caprolactone and p-dioxanone where the mole ratio of ε-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Examples of suitable biocompatible elastomers are described in U.S. Pat. No. 5,468,253.

To form the granules, the biocompatible, bioresorbable polymer or copolymer material is milled to a powder and the particles that are produced serve as the granules. Once milled, the particles or granules can be sieved and sorted by size. An appropriate range of sizes for the granules of the present invention are in the range of about 150 μm to about 600 μm in diameter. As explained in greater detail below, the granules can have an average outer diameter in the range of about 150 to 600 μm, and preferably in the range of about 150 to 300 μm. A bed of these beads or granules can be used to effectively sieve minced tissue fragments from a liquid suspension. The granules with the tissue fragments form a suspension that can be collected and loaded into an injection device for delivery to an injury or diseased tissue site. The granules act as a carrier and also as a scaffold to support new tissue growth. Such a composition can conform to any defect geometry, enabling the implant to assume a shape complementary to that of the implantation site and provide enhanced healing.

In another embodiment of the present invention, the tissue carrier matrix further includes a binding agent that acts to gel together or facilitate cohesion of the tissue fragments and granules, thereby creating a cohesive matrix. The binding agent enables the implant to take on a semi-solid or gel-like form which helps the suspension retain a given geometry while tissue remodeling occurs. For instance, the binding agent could be a gel or biological or synthetic hydrogel so that the implant takes the form of an injectable gel. Suitable materials for the binding agent include shark cartilage, alginate, hyaluronic acid, collagen gel, fibrin glue, fibrin clot, poly(N-isopropylacrylamide), agarose, chitin, chitosan, cellulose, polysaccharides, poly(oxyalkylene), a copolymer of poly (ethylene oxide)-poly(propylene oxide), poly(vinyl alcohol), polyacrylate, platelet rich plasma (PRP) clot, platelet poor plasma (PPP) clot, Matrigel, blood clot, gelatin-resorcin-formalin adhesives, mussel-based adhesives, dihydroxyphenylalanine (DOPA) based adhesives, transglutaminase, poly (amino acid)-based adhesives, cellulose-based adhesives, polysaccharide-based adhesives, synthetic acrylate-based adhesives, liquid and semi-solid fatty acid esters of glycerol and succinic acid (MGSA), MGSA/polyethylene glycol (MGSA/PEG) copolymers, polyvinylpyrolidone (PVP), PVP copolymers, gelatin, albumin, monoglycerides, diglycerides, triglycerides laminin, elastin, proteoglycans, and combinations thereof.

Where a solid or cured implant is desired, a curing agent can additionally be provided with the tissue carrier matrix to allow the injectable implant to set in place at the defect site. This curing agent would act to crosslink the binding agent, thereby forming a solid implant within which are the tissue fragments and the bioresorbable, biocompatible granules. In one aspect, the implant is cured once it is delivered to the implantation site. It is contemplated, however, that the implant can be allowed to cure prior to implantation as well, if so desired. The curing agent should be selected so as to effect crosslinking of the particular binding agent contained in the implant. Suitable curing agents include, for example, proteases such as thrombin, calcium, divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light (e.g., blue light and UV light), pH, temperature, metal ions, and combinations thereof. The present invention contemplates that, by using minced tissue fragments or particles rather than isolated cells, the natural environment of the tissue fragments will provide sufficient protection of the cells against the harsh reagents used for setting the implant.

To further enhance the implant's regenerative or reconstructive abilities, the tissue carrier matrix can also include a biological component such as an effector which enhances the effectiveness of the tissue fragments and facilitates tissue repair and healing of the injured tissue. For example, in yet another embodiment of the present invention, the granules can be formulated to contain an effective molecule that would enhance the activity of the tissue fragments. Thus, the granules function in multiple ways by sieving the tissue fragments, providing a support and carrier for injection delivery to the site, providing a structural support for tissue remodeling, and potentially delivering other enhancing drug therapeutics to the site.

The biological component can be combined with the tissue carrier matrix in a variety of ways. For example, the biological component can be contained inside the granules themselves. For instance, the granules can be porous to allow the biological component to be contained inside the pores. Alternatively, the biological component can be contained in a slow-release coating covering the granules. One skilled in the art will recognize that the biological component can be incorporated into the granules by any suitable manner known in the art that allows the granules to administer the biological component to the minced tissue fragments, without affecting the effectiveness of the biological component.

The biological component can be selected from among a variety of effectors that, when present at the site of injury, promotes healing and/or regeneration of the affected tissue. In addition to being compounds or agents that actually promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED and Surgicel®, available from Ethicon, Inc.), hyaluronic acid, and compounds or agents that suppress the immune system (e.g., immunosuppressants).

By way of example, other types of effectors suitable for use with the implant of the present invention include antibiotics, antimicrobial agents, anti-inflammatory agents, heterologous or autologous growth factors, growth factor fragments, small-molecule wound healing stimulants, proteins (including xenogeneic cartilage and matrix proteins), peptides, antibodies, enzymes, platelets, glycoproteins, hormones, glycosaminoglycans, nucleic acids, analgesics, viruses, virus particles, and cell types. It is understood that one or more effectors of the same or different functionality may be incorporated within the implant.

Examples of suitable effectors include the multitude of heterologous or autologous growth factors known to promote healing and/or regeneration of injured or damaged tissue. These growth factors can be incorporated directly into the biocompatible scaffold, or alternatively, the biocompatible scaffold can include a source of growth factors, such as for example, platelets. Exemplary growth factors include, but are not limited to, TGF-β, bone morphogenic protein, cartilage-derived morphogenic protein, fibroblast growth factor, platelet-derived growth factor, vascular endothelial cell-derived growth factor (VEGF), epidermal growth factor, insulin-like growth factor, hepatocyte growth factor, and fragments thereof. Suitable effectors likewise include the agonists and antagonists of the agents noted above. The growth factor can also include combinations of the growth factors listed above. In addition, the growth factor can be autologous growth factor that is supplied by platelets in the blood. In this case, the growth factor from platelets will be an undefined cocktail of various growth factors. Platelets are normally found in the blood and play a role in hemostasis and wound healing. During clot formation, the platelets become activated and release growth factors such as PDGF, TGF-β, VEGF, and IGF. Platelets can be separated from blood using techniques such as centrifugation. When platelet rich plasma (PRP) is combined with an activator, a platelet clot is created. An activator can be, but is not limited to, thrombin, calcium, adenosine di-phosphate (ADP), collagen, epinephrine, arachidonic acid, prostaglandin E2, ristocetin, calcium, retinoids, ascorbate, antioxidants, and combinations thereof.

The proteins that may be present within the implant include proteins that are secreted from a cell or other biological source, such as for example, a platelet, which is housed within the implant, as well as those that are present within the implant in an isolated form. The isolated form of a protein typically is one that is about 55% or greater in purity, i.e., isolated from other cellular proteins, molecules, debris, etc. More preferably, the isolated protein is one that is at least 65% pure, and most preferably one that is at least about 75 to 95% pure. Notwithstanding the above, one of ordinary skill in the art will appreciate that proteins having a purity below about 55% are still considered to be within the scope of this invention. As used herein, the term "protein" embraces glycoproteins, lipoproteins, proteoglycans, peptides, and fragments thereof. Examples of proteins useful as effectors include, but are not limited to, pleiotrophin, endothelin, tenascin, fibronectin, fibrinogen, vitronectin, V-CAM, I-CAM, N-CAM, selectin, cadherin, integrin, laminin, actin, myosin, collagen, microfilament, intermediate filament, antibody, elastin, fibrillin, tissue inhibitor of metalloproteinases (TIMPs), and fragments thereof.

Glycosaminoglycans, highly charged polysaccharides which play a role in cellular adhesion, may also serve as effectors according to the present invention. Exemplary glycosaminoglycans useful as effectors include, but are not limited to, heparan sulfate, heparin, chondroitin sulfate, dermatan sulfate, keratan sulfate, hyaluronan (also known as hyaluronic acid), and combinations thereof.

The tissue repair implant of the present invention can also have cells incorporated therein. Suitable cell types that can serve as effectors according to this invention include, but are not limited to, osteocytes, osteoblasts, osteoclasts, fibroblasts, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal stem cells, epithelial cells, myoblasts, tenocytes, ligament fibroblasts, neurons, and bone marrow cells. Cells typically have at their surface receptor molecules which are responsive to a cognate ligand (e.g., a stimulator). A stimulator is a ligand which, when in contact with its cognate receptor, induces the cell possessing the receptor to produce a specific biological action. For example, in response to a stimulator (or ligand) a cell may produce significant levels of secondary messengers, like $Ca^{+2}$, which then will have subsequent effects upon cellular processes such as the phosphorylation of proteins, such as (keeping with our example) protein kinase C. In some instances, once a cell is stimulated with the proper stimulator, the cell secretes a cellular messenger usually in the form of a protein (including glycoproteins, proteoglycans, and lipoproteins). This cellular messenger can be an antibody (e.g., secreted from plasma cells), a hormone, (e.g., a paracrine, autocrine, or exocrine hormone), a cytokine, or natural or synthetic fragments thereof.

The tissue implant of the present invention can also be used in gene therapy techniques in which nucleic acids, viruses, or virus particles deliver a gene of interest, which encodes at least one gene product of interest, to specific cells or cell types. Accordingly, the biological effector can be a nucleic acid (e.g., DNA, RNA, or an oligonucleotide), a virus, a virus particle, or a non-viral vector. The viruses and virus particles may be, or may be derived from, DNA or RNA viruses. The gene product of interest is preferably selected from the group consisting of proteins, polypeptides, interference ribonucleic acids (iRNA) and combinations thereof.

Once the applicable nucleic acids and/or viral agents (i.e., viruses or viral particles) are incorporated into the tissue carrier matrix of the tissue repair implant, the implant can then be implanted into a particular site to elicit a type of biological response. The nucleic acid or viral agent can then be taken up by the cells and any proteins that they encode can be produced locally by the cells. In one embodiment, the nucleic acid or viral agent can be taken up by the cells within the tissue fragment of the minced tissue suspension, or, in an alternative embodiment, the nucleic acid or viral agent can be taken up by the cells in the tissue surrounding the site of the injured tissue. One of ordinary skill in the art will recognize that the protein produced can be a protein of the type noted above, or a similar protein that facilitates an enhanced capacity of the tissue to heal an injury or a disease, combat an infection, or reduce an inflammatory response. Nucleic acids can also be used to block the expression of unwanted gene product that may impact negatively on a tissue repair process or other normal biological processes. DNA, RNA and viral agents are often used to accomplish such an expression blocking function, which is also known as gene expression knock out.

One skilled in the art will appreciate that the identity of the biological component may be determined by a surgeon, based on principles of medical science and the applicable treatment objectives.

In an exemplary method of forming the tissue repair implant of the present invention, the biocompatible, bioresorbable polymer or copolymer material is milled to form a powder. The particles of the resultant powder, which serve as the granules of the implant, are then sorted by size. The sorted granules are set aside, while a tissue sample containing viable cells is obtained. The tissue sample is minced, producing a fluid suspension containing the minced tissue fragments. The fluid suspension is then introduced to a bed of the granules of a selected range of sizes. The bed of granules functions to sieve the fluid suspension, separating the fluid from the tissue fragments, resulting in a slurry or suspension containing both the granules and the tissue fragments. The slurry, which forms the tissue repair implant, can then be collected and inserted into a delivery device such as an injection device for immediate delivery to an injury or diseased tissue site. The tissue fragments serve as a cell source for new cellular growth, and have an effective amount of viable cells that can migrate out of the tissue fragment to populate the tissue carrier matrix once the implant is delivered to the patient. The granules serve as a microcarrier to provide sufficient mechanical integrity for cellular integration with the surrounding environment during the tissue remodeling process. Because the implant is in a suspension form, the implant can conform to any defect geometry and assume a shape complementary to that of the implantation site. The close interface between the injected implant and the tissue site thus enhances tissue repair and healing.

If desired, the tissue carrier matrix can also include a binding agent that acts to gel together the tissue fragments and granules and thereby form a cohesive matrix. The binding agent can be added to the matrix to enable the implant to take on a gel-like or semi-solid form which enhances retention of the implant at the tissue site while tissue remodeling is occurring. Where a solid or cured implant is desired, a curing agent can additionally be provided with the tissue carrier matrix. This curing agent would act to crosslink (i.e., form covalent bonds with) the binding agent, thereby forming a solid implant within which are the tissue fragments and the bioresorbable, biocompatible granules. In one aspect, the curing agent is added to the implant after delivery to the implantation site so that the implant is set after delivery. In another aspect, the curing agent is added prior to delivery of the implant to the site, resulting in a cured implant being delivered.

To further enhance the implant's regenerative or reconstructive abilities, the tissue carrier matrix can also include a biological component or effector which enhances the effectiveness of the tissue fragments to new cellular growth. In an exemplary method for incorporating the biological component, the tissue carrier matrix can be placed in a suitable container comprising the biological component prior to surgical placement at the tissue site. After an appropriate time and under suitable conditions, the granules can become impregnated with the biological component. Following surgical placement, an implant in which the tissue carrier matrix is devoid of any biological component can be infused with biological agent(s), or an implant in which the matrix includes at least one biological component can be augmented with a supplemental quantity of the biological component. Another exemplary method of incorporating a biological component within a surgically installed implant is by injection using an appropriately gauged syringe.

The amount of the biological component included with the tissue repair implant will vary depending on a variety of factors, including the size of the injury or defect site, the identity of the biological component, and the intended purpose of the tissue repair implant. One skilled in the art can readily determine the appropriate quantity of biological component to include within an implant for a given application in order to facilitate and/or expedite the healing of tissue. The amount of biological component will, of course, vary depending upon the identity of the biological component and the given application.

It is also possible to add solids (e.g., barium sulfate) that will render the tissue implants radio opaque. The solids that may be added also include those that will promote tissue regeneration or regrowth, as well as those that act as buffers, reinforcing materials or porosity modifiers.

The tissue repair implant can be used in the treatment of a tissue injury, such as injury to a ligament, tendon, nerve, skin, cartilage or meniscus. Repairing tissue injuries involves the steps of obtaining a sample of living tissue by any of the variety of techniques known to those skilled in the art, preferably by biopsy or other minimally invasive techniques. The sample of living tissue is then processed under sterile conditions to create at least one minced, finely divided tissue particle, combining the tissue fragment with a plurality of biocompatible, bioresorbable granules to form a suspension of tissue and granules, and injecting the suspension at a tissue injury site to deliver the tissue repair implant to the tissue injury. Additionally, the tissue repair implant can be allowed to set or cure into a shape complementary to the geometry of the defect site. In the alternative, it is contemplated that the suspension can also be introduced into a mold and allowed to set prior to implantation at the defect site. The mold can have a geometry and dimension matching that of the defect site. It is contemplated that a specialized surgical tool can be used to prepare the defect area so that the implantation site has a defined geometry. Once cured, the implant can be further trimmed and shaped as necessary before implantation.

In an exemplary method of repairing tissue using the implant of the present invention, a patient diagnosed with a symptomatic articular cartilage defect is prepped for arthroscopic surgery. The surgeon then harvests healthy cartilage tissue from a non-weight bearing area of the patient's joint using a harvesting instrument. Preferably, the instrument also allows the surgeon to mince the cartilage tissue and collect the minced tissue fragments in a separate chamber of the instrument which is preloaded with the milled granules. Next, the surgeon can inject a binding agent such as a biological glue into the chamber to prepare a mixture containing the cartilage fragments, granules and binding agent. A curing agent can also be introduced to the chamber at this time. While the mixture is being prepared, careful debridement of the affected area can be performed to remove unhealthy tissue from the cartilage defect and prepare the area to receive the mixture. The formed mixture can then be loaded into an injection device such as a specialized syringe to arthroscopically inject the mixture into the affected area. After injection, the mixture can be shaped or sculpted to fill the defect area and the surrounding tissue before the mixture has cured. Once cured, the arthroscopic ports can be sutured closed, and the patient can then begin a controlled rehabilitation program.

The methods of repairing tissue injuries using the tissue implants according to the present invention can be conducted during a surgical procedure to repair the tissue injury. Alternatively, the steps of processing the tissue sample to create minced, finely divided tissue particles, depositing the tissue particles upon the scaffold to form a tissue repair implant, and/or incubating the tissue repair implant prior to implantation can be conducted at another, sterile location prior to surgical placement of the implant relative to the site of injury.

The following example is illustrative of the principles and practice of this invention. Numerous additional embodiments within the scope and spirit of the invention will become apparent to those skilled in the art.

Example

The primary objective of this study was to examine the outgrowth of chondrocytes in a sample implant comprising bovine cartilage fragments, fibrin glue and polyglycolic acid (PGA) granules in vitro. For the study, minced bovine cartilage and PGA granules of different sizes were mixed with fibrin glue (Tisseel™) and injected into a mold to form bioadhesive plugs in accordance with Table 1 below. The resulting plugs were then cultured in cell culture or chondrogenic medium for 3 and 6 week periods, respectively. After incubation, the plugs were fixed, sectioned and stained with hematoxylin and eosin (H & E).

TABLE 1

Experimental Conditions for Study of Chondrocyte Outgrowth from Composite Mold Containing Fibrin Glue, PLA Granules, and Bovine Cartilage Fragments

| Conditions | Amount of minced cartilage | Amount of PGA | Amount of fibrin glue | Incubation period 3 & 6 weeks |
|---|---|---|---|---|
| Composite plug with PGA (158 µm) granules | 100 mg | 31 mg | 400 µl | n = 1 each |
| Composite plug with PGA (286 µm) granules | 100 mg | 31 mg | 400 µl | n = 1 each |
| Composite plug with PLA (633 µm) granules | 100 mg | 31 mg | 400 µl | n = 1 each |
| Fibrin glue plug only | 100 mg | 0 mg | 400 µl | n = 1 each |

Results

Figure 1A:
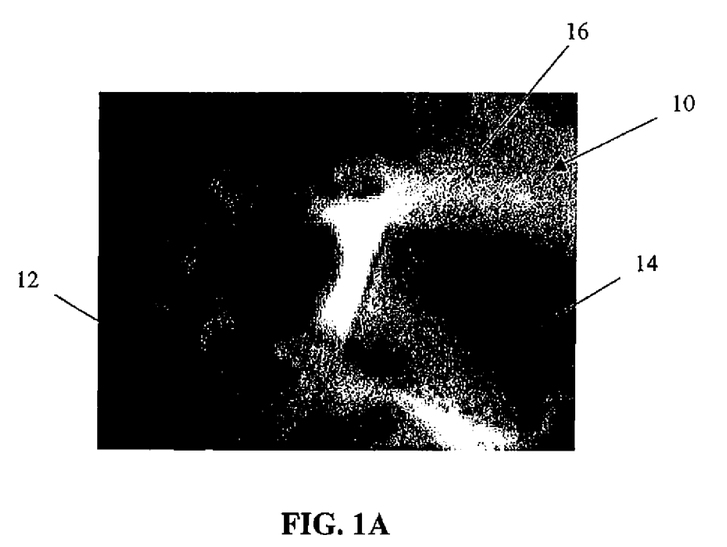
FIG. 1A is a photomicrograph showing a section of one embodiment of the tissue repair implant which comprises cartilage fragments, 158 μm PGA granules, and fibrin glue in accordance with the present invention.
Figure 1B:
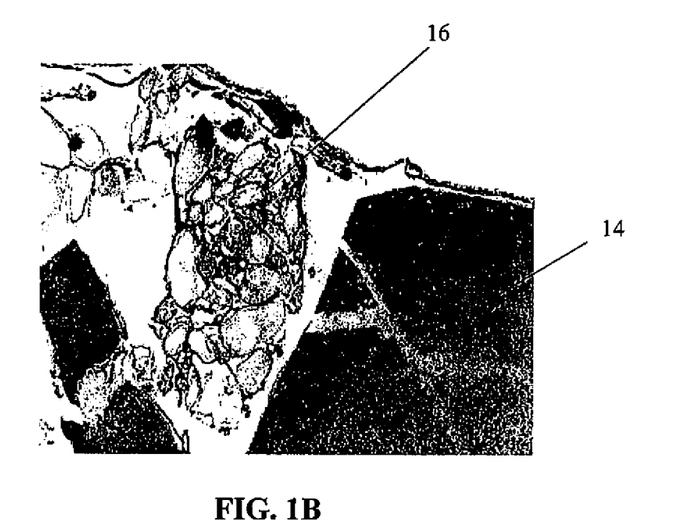
FIG. 1B is a photomicrograph of a histological section of an implant similar to FIG. 1A, after 3 weeks in vitro.
Figure 1C:
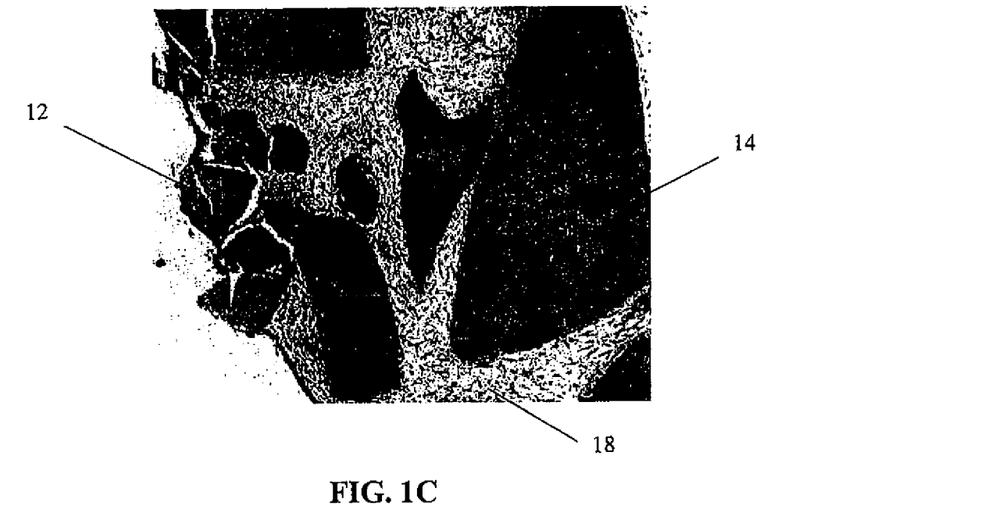
FIG. 1C is a photomicrograph of a histological section of an implant similar to FIG. 1A, after 6 weeks in vitro.
Figure 1D:
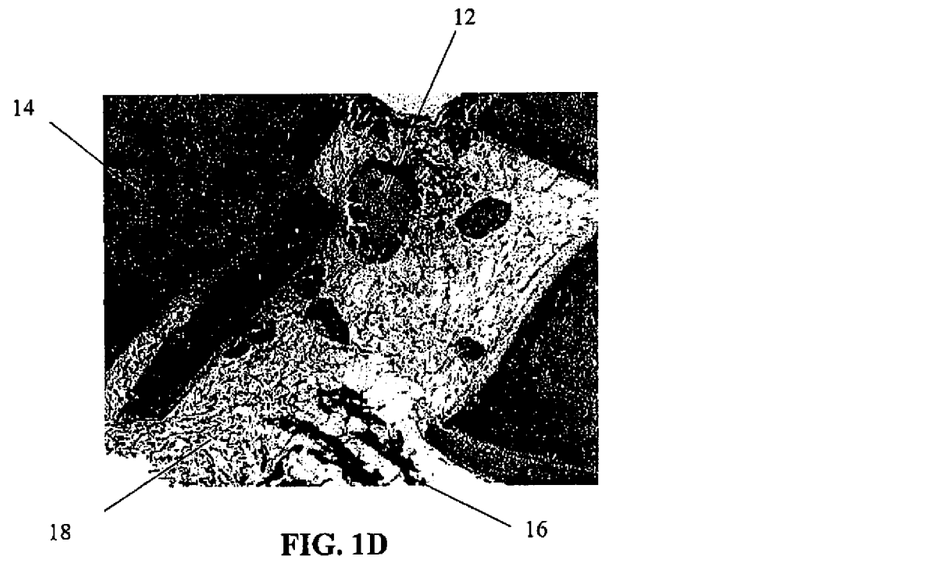
FIG. 1D is yet another photomicrograph of a histological section of the implant of FIG. 1C.

FIG. 1A shows a photomicrograph of a composite plug 10 with PGA granules 12 of approximately 158 µm diameter and cartilage pieces 14 in fibrin glue 16, made in accordance with the first condition of Table 1. FIG. 1B shows a histological section of a composite plug in accordance with the first condition of Table 1, H & E stained, after 3 weeks. Slight cell growth is seen. After 6 weeks, however, the PGA granules show some resorption while the fibrin glue also indicates absorption and/or degradation. As further shown in FIGS. 1C and 1D, which are histological sections of a composite plug made in accordance with the first condition of Table 1, H & E stained, after 6 weeks, there appears to be chondrocyte outgrowth 18 around the cartilage fragments 14.

Figure 2A:
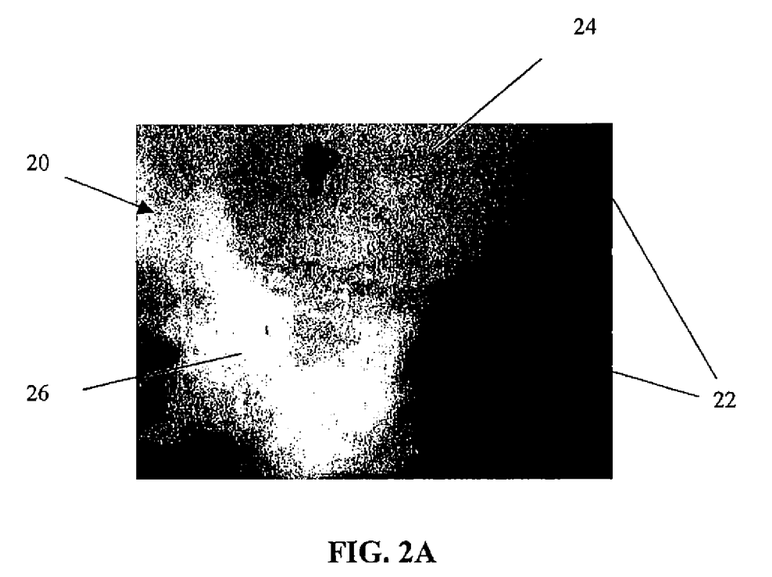
FIG. 2A is a photomicrograph of a histological section of another embodiment of the tissue repair implant comprising cartilage fragments, 286 μm PGA granules, and fibrin glue in accordance with the present invention.
Figure 2B:
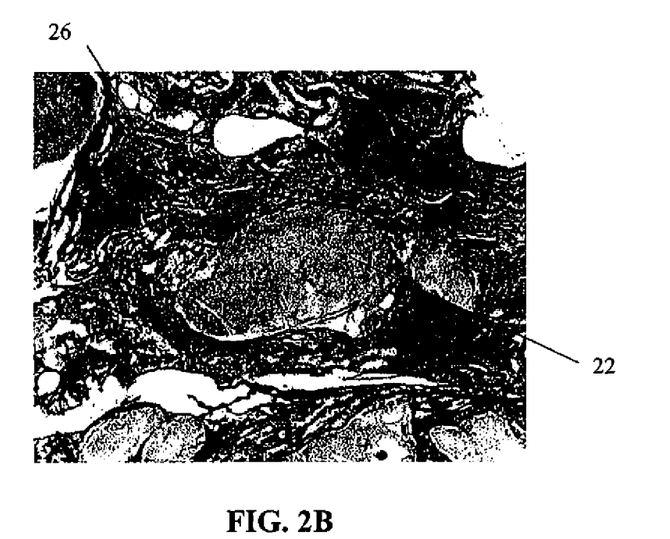
FIG. 2B is a photomicrograph of a histological section of an implant similar to FIG. 2A, after 3 weeks in vitro.
Figure 2C:
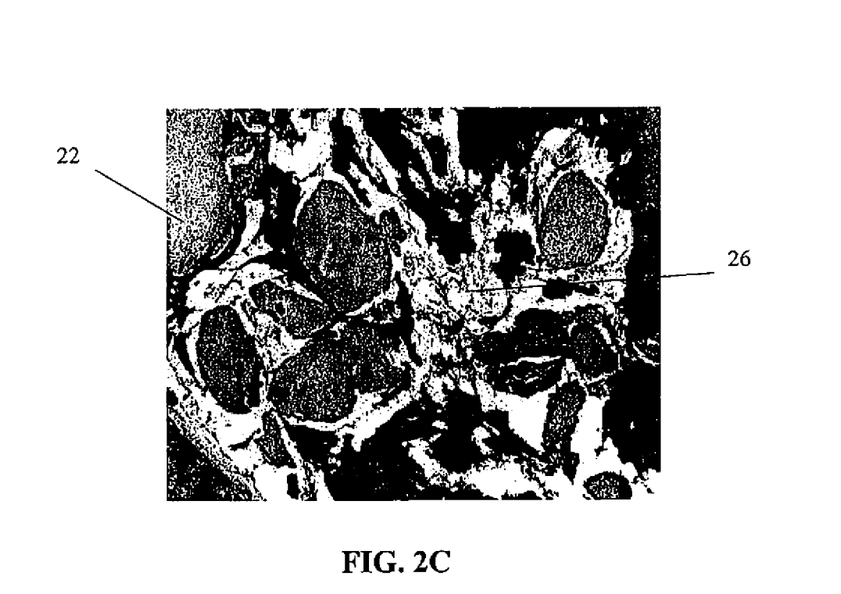
FIG. 2C is a photomicrograph of a histological section of an implant similar to FIG. 2A, after 6 weeks in vitro.
Figure 2D:
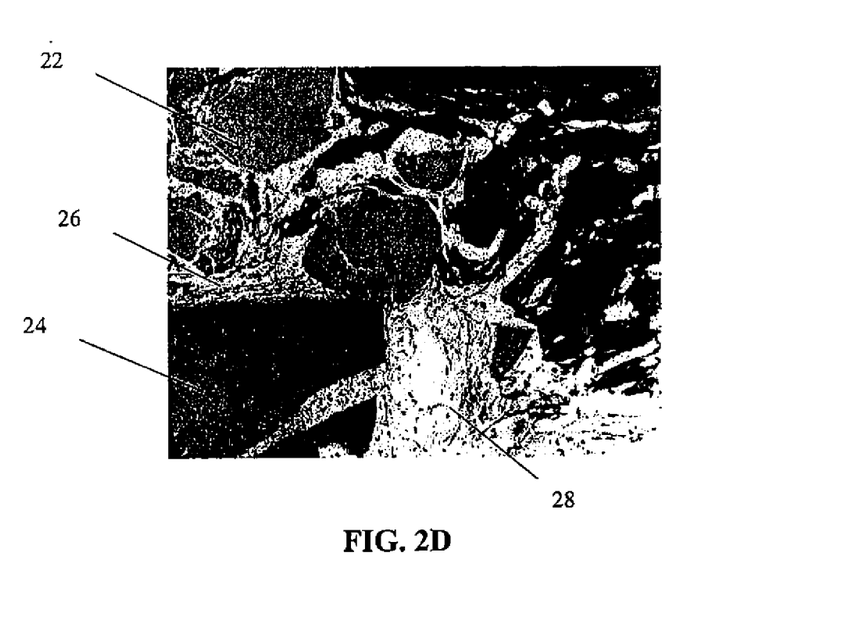
FIG. 2D is yet another photomicrograph of a histological section of the implant of FIG. 2C.

FIG. 2A shows a photomicrograph of a composite plug 20 with PGA granules 22 of approximately 286 μm diameter and cartilage pieces 24 in fibrin glue 26, made in accordance with the second condition of Table 1. FIG. 2B shows a histological section of a composite plug in accordance with the second condition of Table 1, H & E stained, after 3 weeks. Similar to FIG. 1B, slight cell growth is seen. After 6 weeks, however, the PGA granules show some resorption while the fibrin glue also indicates absorption and/or degradation. As further shown in FIGS. 2C and 2D, which are histological sections, H & E stained, after 6 weeks of a composite plug made in accordance with the second condition of Table 1, there appears to be chondrocyte outgrowth 28 around the cartilage fragments 24.

Figure 3A:
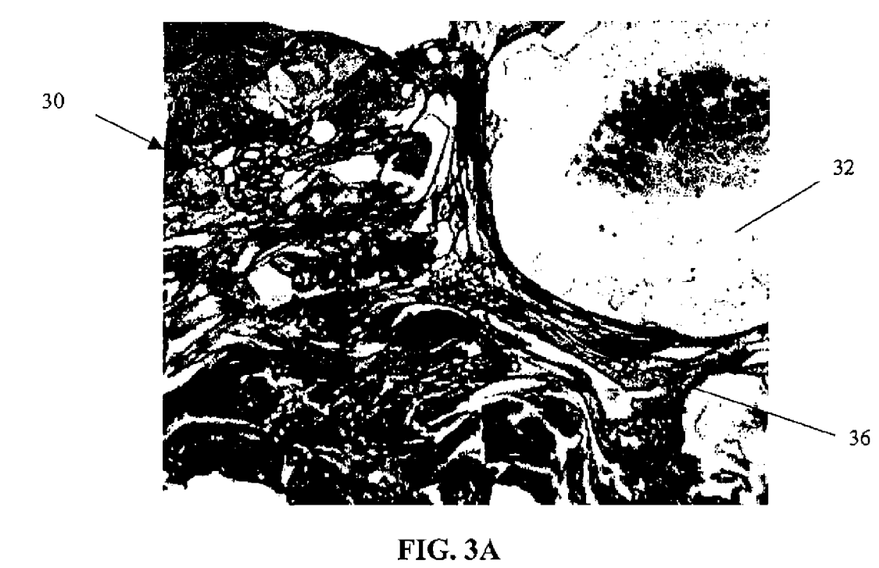
FIG. 3A is a photomicrograph of a histological section at 100× magnification of yet another embodiment of a tissue repair implant comprising cartilage fragments, 633 µm PLA granules and fibrin glue, after 3 weeks in vitro.
Figure 3B:
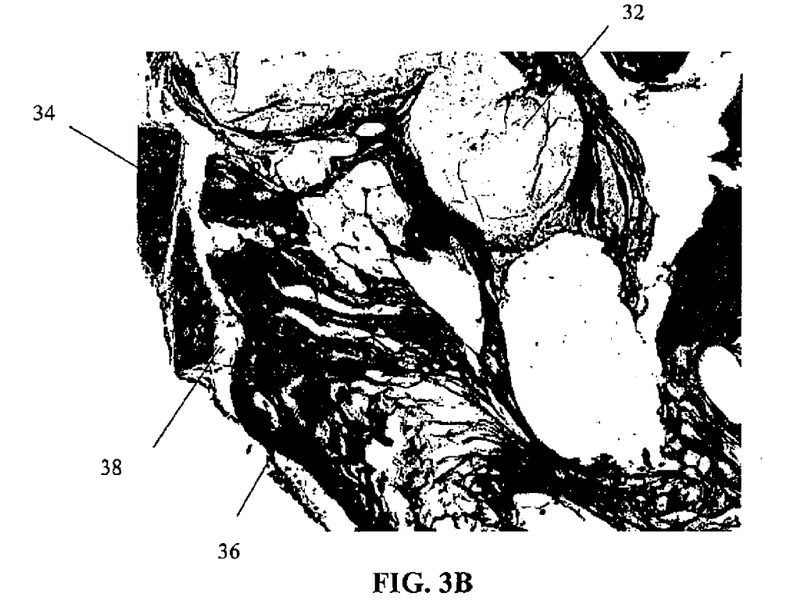
FIG. 3B is a photomicrograph of a histological section at 100× magnification of a tissue repair implant similar to FIG. 3A, after 6 weeks in vitro.

FIG. 3A shows a histological section of a composite plug 30 made in accordance with the third condition of Table 1, containing cartilage fragments 34 and PLA granules 32 of approximately 633 μm diameter embedded in fibrin glue 36, stained with H & E after 3 weeks, at 100× magnification. FIG. 3B shows a histological section of the composite plug 30 after 6 weeks. As shown, there is some outgrowth of chondrocytes 38 around the granules 32 and glue 36 after 6 weeks.

Figure 4A:
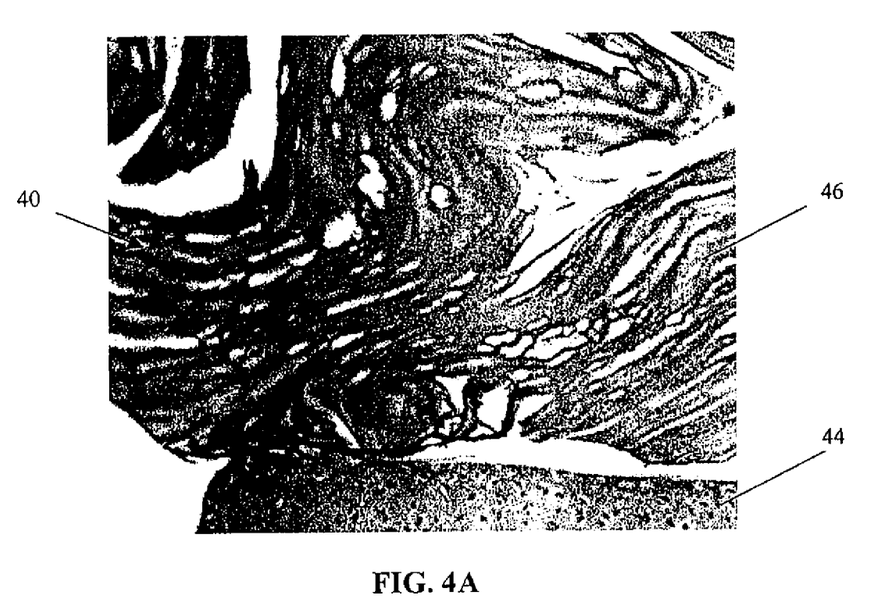
FIG. 4A is a photomicrograph of a histological section at 100× magnification of a tissue repair implant comprising cartilage fragments and fibrin glue, after 3 weeks in vitro.
Figure 4B:
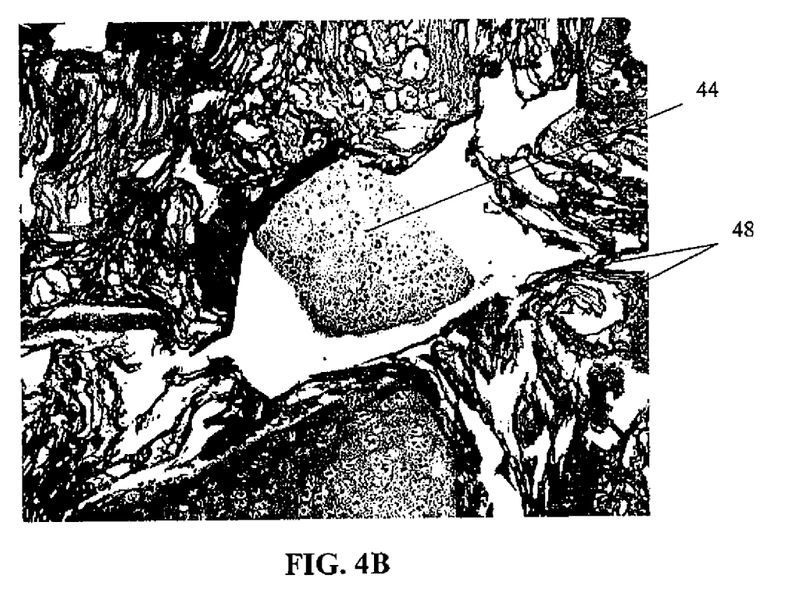
FIG. 4B is a photomicrograph of a histological section at 100× magnification of a tissue repair implant similar to FIG. 4A, after 6 weeks in vitro.

Finally, FIGS. 4A and 4B show histological sections of a composite plug 40 made in accordance with the fourth condition of Table 1, containing cartilage fragments 44 embedded in fibrin glue 46, stained with H & E after 3 weeks and 6 weeks, respectively, at 100× magnification. At 6 weeks, FIG. 4B shows some cell outgrowth.

Based on the results of the study, it can be concluded that bovine chondrocytes from minced cartilage were able to migrate in and around the fibrin glue bioadhesive plug within 6 weeks. It further appears that the presence of the polyglycolic acid (PGA) granules embedded within the fibrin glue plugs facilitated the migration process. Finally, it appears that the smaller sized PGA granules (mean particle diameter 158 μm and 286 μm) were more effective in facilitating cell attachment and in inducing cellular migration to contribute to the overall tissue remodeling process.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A tissue repair implant, comprising:
   a tissue carrier matrix in the form of an injectable suspension, the tissue carrier matrix comprising a plurality of biocompatible, bioresorbable granules and at least one tissue fragment in association with the tissue carrier matrix, the at least one tissue fragment having an effective amount of viable cells that can migrate out of the tissue fragment and populate the tissue carrier matrix;
   wherein the at least one tissue fragment has a particle size in the range of about 0.1 to about 2 mm$^3$;
   wherein each of the plurality of granules have an average outer diameter in a range of about 150 to about 300 μm; and
   wherein the at least one tissue fragment is cohesive with the granules within said tissue carrier matrix.

2. The implant of claim 1, wherein the plurality of granules is configured to sieve the at least one tissue fragment from a solution.

3. The implant of claim 1, wherein the at least one tissue fragment has a particle size in the range of about 0.1 to about 2 mm$^3$.

4. The implant of claim 1, wherein the granules comprise at least one of aliphatic polyesters, copoly(ether-esters), solid copolymers of fatty acid esters of glycerol and succinic acid, polyoxaesters, collagen, gelatin, albumin, hyaluronate, glycosaminoglycans, polyanhydrides, polysaccharides, polyphosphazines, subintestinal mucosa, and acellular tissues.

5. The implant of claim 1, wherein the at least one tissue fragment is obtained from a connective tissue type selected from the group consisting of cartilage, meniscus, tendon, ligament, dermis, bone, fat, synovial tissue, muscle tissue, and combinations thereof.

6. The implant of claim 1, wherein the tissue carrier matrix comprises at least one of a proteoglycan, heparan sulfate, heparin, chondroitin sulfate, dermatan sulfate, keratan sulfate, and hyaluronan.

7. The implant of claim 1, wherein the at least one tissue fragment comprises a tissue selected from the group consisting of autogeneic tissue, allogeneic tissue, xenogeneic tissue, and combinations thereof.

8. The implant of claim 1, wherein the granules comprise an aliphatic polyester selected from the group consisting of homopolymers or copolymers of lactides, glycolides, 8-caprolactone, p-dioxanone (1,4-dioxan-2-one), trimethylene carbonate (1,3-dioxan-2-one), and combinations thereof.

9. The implant of claim 1, wherein the tissue carrier matrix further comprises at least one biological component selected from the group consisting of antibiotics, antimicrobial agents, anti-inflammatory agents, growth factors, growth factor fragments, small-molecule wound healing stimulants, hormones, cytokines, proteins, peptides, antibodies, enzymes, isolated cells, glycosaminoglycans, immunosuppressants, nucleic acids, analgesics, platelets, an activator of platelets, viruses, virus particles, and combinations thereof.

10. The implant of claim 1, wherein the at least one biological component is an isolated cell selected from the group consisting of osteocytes, fibroblasts, stem cells, pluripotent cells, chondrocyte progenitors, chondrocytes, osteoclasts, osteoblasts, endothelial cells, macrophages, adipocytes, monocytes, plasma cells, mast cells, umbilical cord cells, leukocytes, stromal cells, mesenchymal stem cells, epithelial cells, myoblasts, tenocytes, ligament fibroblasts, and bone marrow cells.

11. The implant of claim 1, further including a binding agent in association with the tissue carrier matrix.

12. The implant of claim 1, wherein the binding agent is selected from the group consisting of shark cartilage, alginate, hyaluronic acid, collagen gel, fibrin glue, fibrin clot, poly(N-isopropylacrylamide), agarose, chitin, chitosan, cellulose, polysaccharides, poly(oxyalkylene), a copolymer of poly(ethylene oxide)-poly(propylene oxide), poly(vinyl alcohol), polyacrylate, platelet rich plasma (PRP) clot, platelet poor plasma (PPP) clot, Matrigel, blood clot, gelatin-resorcin-formalin adhesives, mussel-based adhesives, dihydroxyphenylalanine (DOPA) based adhesives, transglutaminase, poly(amino acid)-based adhesives, cellulose-based adhesives, polysaccharide-based adhesives, synthetic acrylate-based adhesives, liquid and semi-solid fatty acid esters of glycerol and succinic acid (MGSA), MGSA/polyethylene glycol (MGSA/PEG) copolymers, polyvinylpyrolidone (PVP), PVP copolymers, gelatin, albumin, monoglycerides, diglycerides, triglycerides laminin, elastin, proteoglycans, and combinations thereof.

13. The implant of claim 8, further including a curing agent that crosslinks the binding agent to enable the implant to set.

14. The implant of claim 1, wherein the curing agent is selected from the group consisting of thrombin, calcium, divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light, pH, temperature, metal ions, and combinations thereof.

15. The implant of claim 1, wherein the at least one biological component comprises platelets, and further includes an activator of platelets.

16. The implant of claim 1, wherein the activator of platelets is selected from the group consisting of thrombin, calcium, adenosine di-phosphate (ADP), collagen, epinephrine, arachidonic acid, prostaglandin, ristocetin, retinoids, ascorbate, antioxidants, and combinations thereof.

17. A tissue repair implant, comprising a tissue carrier matrix comprising:
   a plurality of biocompatible, bioresorbable granules;
   at least one tissue fragment having an effective amount of viable cells that can migrate out of the tissue fragment and populate the tissue carrier matrix; and
   a binding agent,
   wherein the at least one tissue fragment, granules, and binding agent form a cohesive matrix that is in the form of an injectable suspension; and wherein each of the plurality of granules have an average outer diameter in a range of about 150 to about 300 μm.

18. The tissue repair implant of claim 16, wherein the binding agent is a fibrin glue.

* * * * *